United States Patent [19]

Jones

[11] 4,202,349
[45] May 13, 1980

[54] RADIOPAQUE VESSEL MARKERS

[76] Inventor: James W. Jones, 4108 James Dr., Metairie, La. 70003

[21] Appl. No.: 899,292

[22] Filed: Apr. 24, 1978

[51] Int. Cl.² ............................................. A61B 19/00
[52] U.S. Cl. ...................................... 128/689; 3/1.4;
128/1 R
[58] Field of Search ................ 128/1.1, 1.2, 1 R, 2 R,
128/2 A, 2.05 R, 2.05 P, 330, 335.5, 334 R, 654,
667, 687, 689, 691; 3/1.4

[56] References Cited

U.S. PATENT DOCUMENTS

| | | |
|---|---|---|
| 2,109,780 | 3/1938 | Mott . |
| 3,155,091 | 11/1964 | Nissenbaum et al. ............... 128/2 W |
| 3,194,239 | 7/1965 | Sullivan ............................. 128/335.5 |
| 3,812,842 | 5/1974 | Rodriguez ........................... 128/2 A |
| 4,022,190 | 5/1977 | Meyer ................................. 128/2 A |
| 4,041,931 | 8/1977 | Elliott et al. ........................ 128/1 R |

Primary Examiner—Robert W. Michell
Assistant Examiner—C. F. Rosenbaum
Attorney, Agent, or Firm—Keaty and Garvey

[57] ABSTRACT

A radiopaque blood vessel marker is provided for attachment to the side wall portions of a blood vessel during, for example, a coronary by-pass operation. The markers in the preferred embodiment are flattened, oval-shaped radiopaque discs which are attached to the outer peripheral wall portion of the blood vessel at one hundred eighty degrees (180°) with respect to one another (See FIG. 3). Each radiopaque marker can be comprised of a central imbedded element of radiopaque material such as tantilum which is surrounded by a suitable plastic or like resinous material which is inert and acceptable for use within the human body. During a coronary by-pass, for example, these markers could be attached by suturing or like means to the vein graft which is itself sutured into its new position during the by-pass operation. A fluoroscopic examination by a radiologist would reveal a desirable pulsation of the graft vessel in the form of the two attached markers as the radiopaque markers will constantly move (in and out) with respect to one another. Each marker is attached to the undulating wall portion of the vessel which is constantly moved when blood flow is passing through the graft as is desirable. In the event that complications arise, and the graft becomes clotted (stopping the flow of blood therethrough), a fluoroscopic examination will reveal that the radiopaque vessel markers do not move in and out with respect to one another but rather are stationary indicating a lack of undulation and a corresponding lack of blood flow.

25 Claims, 6 Drawing Figures

RADIOPAQUE VESSEL MARKERS

BACKGROUND OF THE INVENTION

1. Field of the Invention

The present invention relates to medical appliances and instruments. More particularly, the present invention relates to radiopaque markers which can be attached to the outer wall portions of a vessel, the markers being of such a radiopaque nature allow inspection of their respective position by fluoroscopic examination, thus indicating the desirable pulsation of blood vessel or artery walls to which they are attached.

2. General Background and Prior Art

During certain surgical operations involving the circulatory system of a patient, portions of the circulatory system are removed from legs and grafted to the patient in the heart region. Operations of this type are known in the art as a coronary bypass. The "graft" can be a vein surgically removed from a portion of the leg and then sutured into its desirable position as is known in the art.

Complications can arise if the graft becomes clotted with blood and cannot convey the amount of blood therethrough as is desirable. If a surgeon is suspicious that such a blockage has occurred, he must now investigate the blockage by means of a complicated procedure using a catheter and injecting dye into the patient. The dye injected into the vessels will allow them to be viewed by a fluoroscope or like device during a fluoroscopic examination thereby allowing the doctor to determine whether or not the vessel has collapsed or is in fact satisfactorily conveying blood.

The catherization of a patient in this manner is time consuming, expensive, and entails a certain risk to the patient. Hospitalization of the patient is required.

Therefore, a need exits for a simple and inexpensive manner for providing a means of checking a patient at any desirable time to determine whether or not his graft (which was earlier applied during a coronary bypass or like operation) is still functioning properly and conveying blood as is desirable.

GENERAL DESCRIPTION OF THE PRESENT INVENTION

The present invention solves all the prior art problems and shortcomings by providing a radiopaque vessel or artery marker attachable to the outer vessel wall. The vessel marker can be in the form of a substantially flattened disc having means for attaching the disc to the vessel. In the preferred embodiment, a pair of discs could be attached at roughly one hundred eighty degrees (180°) with respect to one another around the vessel or graft. These two disc-like marker bodies are sutured into place on the graft by the surgeon during the coronary bypass operation. Thereafter, they provide a permanent indicator of the outer vessel wall position which position can quickly be observed by a mere fluoroscopic examination. Thus, a patient who has had a coronary bypass operation can be checked promptly, quickly and inexpensively with little risk to the patient by means of a fluoroscopic examination wherein the surgeon, radiologist, or attending physician would merely observe the patient's chest and examine the two radiopaque discs to see if their respective movements were indicative of blood flowing through the graft in a desirable fashion.

As is known in the art, the walls of a vessel will "pulsate" or move with respect to the central bore of the vessel as blood is being pumped by the heart therethrough. This enlargement of each vessel and subsequent contraction will cause the radiopaque markers to appear to move closer and farther apart sequentially as blood is pumped through the vessel to which they are attached. Such a desirable pulsation and accompanying relative movement of each marker body with respect to the other would indicate to the surgeon, radiologist, or attending physician during a fluoroscopic examination that blood is flowing through the artery as desired. With such a cornary marker, no catheterization or other surgical procedure would be necessary in order to examine the patient properly. Indeed, a surgeon could merely have his patients report in to his office on a periodical basis (removing the need for a hospital visit) and do a quick and simple fluoroscopic examination of the area to which the graft was applied and examine the two attached radiopaque marker bodies to see if their movement was oscillating with respect to one another from a farther position to a closer position. If such movement was apparent, the surgeon could be assured that the vessel was expanding and contracting responsive to the flow of blood therethrough in a desirable manner.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

Figure 1:
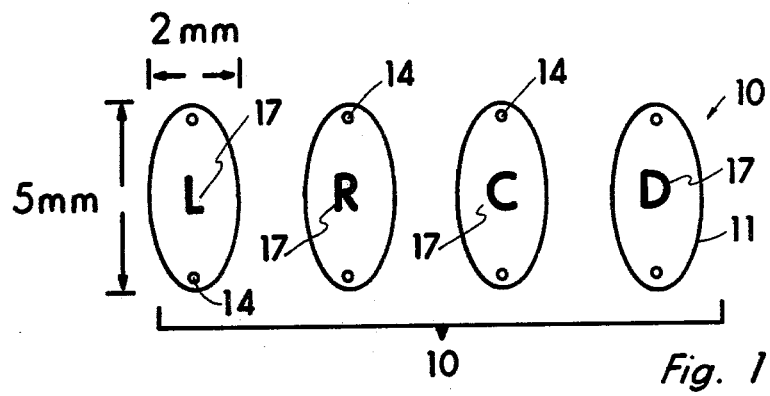
FIG. 1 is a top view of the preferred embodiment of the apparatus of the present invention illustrating a plurality of radiopaque artery markers.

In FIG. 1, there can be seen a plurality of artery markers 10. Each artery marker 10 is comprised of a marker body 11 having openings 14 therethrough which openings provide a means for attaching each respective marker body 11 to a vessel wall 23 as will be described more fully hereinafter. In FIG. 1, artery markers 10 are shown to have a marker body dimension of approximately 5 millimeters in length by 2 millimeters in width, with an oval-shaped marker body 11 being illustrated in the preferred embodiment. It should be understood that similar shapes and similar radiopaque bodies and structures would suffice within the teaching of the present invention. Note that indicia markings 17 could be provided on each marker 10 as an aid to the surgeon as to the proper position to locate the respective marker body 11. In FIG. 1, the letters L and R, for example, indicate left and right which would provide indicia for illustrating to the physician that these two markings 11 would be attached to the left and right portion of vessel 20 respectively, while C and D could indicate "circumflex" and "descending" respectively.

Figure 2:
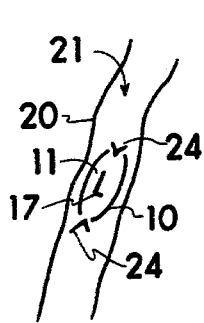
FIG. 2 is a schematic perspective view of a typical blood vessel with a radiopaque marker of the present invention attached thereto.
Figure 3:
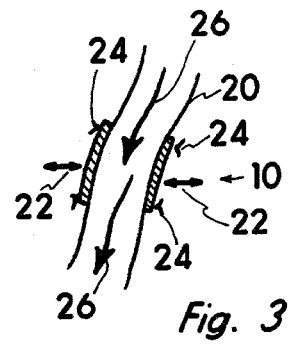
FIG. 3 is a sectional view of the preferred embodiment of the apparatus of the present invention illustrating the connection of two radiopaque markers to a typical vein structure.

FIGS. 2 and 3 illustrate the attachment of artery markers 10 to a typical vessel 20 or like blood conveying vein, artery or like "vessel-like" anatomical structure within the human body. FIG. 2, note that artery marker 10 has been attached by means of sutures 24 applied through openings 14 at the peripheral edge portion of each marker body 11. Note that the artery marker 10 can be attached to vessel 20 on its outer surface 21 by means of surgical sutures 24. The surgeon performing the bypass operation could thus easily attach the markers 10 during the bypass surgical procedure itself.

In FIG. 3, a sectional view of the attachment of two artery markers 10 is illustrated. In the preferred embodiment, a pair of markers 10 would be attached to illustrate the relative movement of the walls 23 (see FIG. 4) of each vessel 20 to which the markers 10 were attached. In FIG. 3, this relative movement would be inward and outward as is illustrated by arrows 22. Arrows 26 in FIG. 3 illustrate the flow of blood through the inner portion of each vessel 20.

Figure 4:
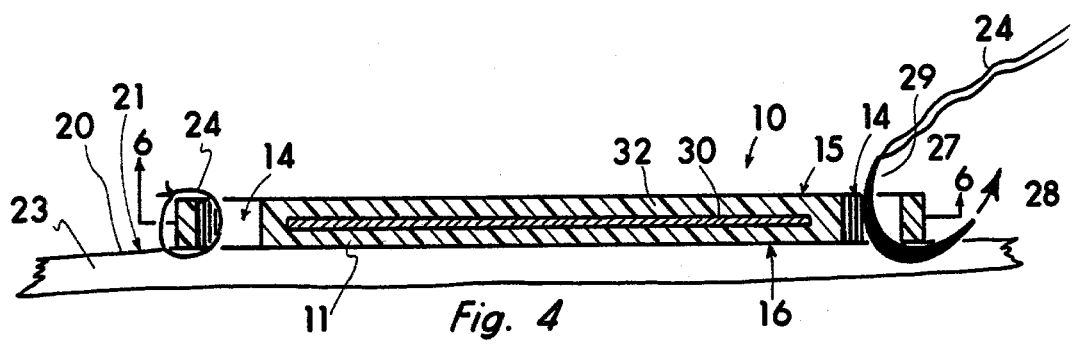
FIG. 4 is a sectional view of the preferred embodiment of the apparatus of the present invention.
Figure 6:
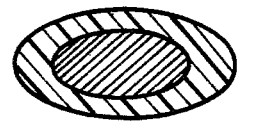
FIG. 6 is a sectional view taken along lines 6—6 of FIG. 4.

FIG. 4 illustrates the preferred embodiment of the apparatus of the present invention and its method of attachment to vessel wall 23. In FIG. 4, there is seen an artery marker designated generally by the numeral 10. Marker 10 is comprised of a marker body 11 which is provided with a central inner radiopaque member 30 which can be, for example, a suitable radiopaque metal such as tantilum (See FIG. 6). Surrounding and embedding this central inner radiopaque member 30 is an outer covering 32. Covering 32 can be, for example, a suitable inert plastic or like resinous material. Such plastic inert materials are known in the medical arts and are generally known and provided as approved plastics for use within the human body by the Federal Food and Drug Administration. Each marker 10 is provided with an upper surface 15 and a lower surface 16. Note that the lower surface 16 is attached to the surface 21 of each vessel 20, with the vessel wall 23 being schematically illustrated in FIG. 4. A pair of openings 14 provice a means for the attachment of sutures 24 therethrough and into a portion of the vessel wall 23. Each suture 24 can be applied by means of a surgical needle 27, with the suture 24 being shown threaded through needle 27 at the needle eye 29. Arrow 28 schematically illustrates the surgical suturing of a suture 24 or other suitable tie such as silk for attaching artery marker 10 to the vessel wall 23. Such a surgical attachment of marker 10 to the vessel wall 23 could be performed by the surgeon simultaneously with the removal of the graft vein from the leg or vessel 20 during the arterial bypass operation. Indeed, markers 10 could be applied before the graft was sutured into its position.

Figure 5:
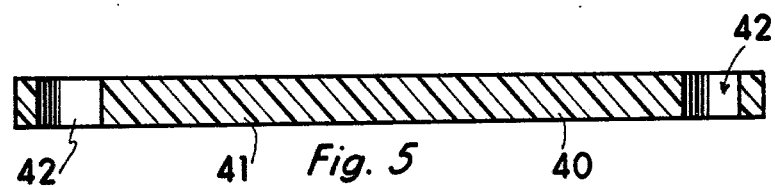
FIG. 5 is a sectional view of an alternative embodiment of the apparatus of the present invention.

In FIG. 5, is seen an alternative embodiment of the apparatus of the present invention designated generally by the numeral 40. Artery marker 40 would be entirely of a plastic or like resinous material, providing a marker body 41 and a plurality of openings 42 for the attachment of the marker body 41 to the vessel wall 23 as was afore described with respect to the preferred embodiment.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A radiopaque vessel marker comprising:
   a. radiopaque marker means adapted for surgical attachment to a portion of an interior blood vessel for indicating the pulsatile flow of blood through the vessel said means providing spaced portions for indicating relative movement with respect to one another during such pulsitile blood flow, said marker means being of a substantially radiopaque material; and
   b. means associated with said marker means for attaching said marker means to the interior blood vessel.

2. The vessel marker of claim 1 wherein said radiopaque means is attached to the outer surface portion of an interior blood vessel.

3. The vessel marker of claim 1 wherein said marker means is a pair of substantially flattened discs adapted for attachment to opposite outer wall portions of a blood vessel.

4. The vessel marker of claim 3 wherein each of said discs is provided with identifying indicia thereon.

5. The vessel marker of claim 3 wherein said attachment means is comprised of at least one opening through said disc, and suture means insertable through said opening and a portion of the vessel for tying said disy to the vessel at said opening.

6. A method of fluoroscopically inspecting a vessel like structure within the human body comprising the steps of:
   a. attaching a pair of spaced radiopaque markers to the outside peripheral wall portion of the vessel-like structure the pair of markers adapted for relative movement with respect to one another; and
   b. examining fluoroscopically the relative movement of each spaced radiopaque marker attached to the vessel-like structure responsive to pulsatile blood flow therethrough.

7. The method of claim 6, wherein in step "a" each radiopaque body is surgically attached to the outside peripheral wall portion of the vessel-like structure.

8. The method of claim 6 wherein in step "a" two radiopaque bodies are surgically attached by suturing to the vessel-like structure.

9. The method of claim 6 wherein in step "a" the pair of radiopaque markers are attached to the outer peripheral wall portion of a blood vessel at opposite sides thereof.

10. The method of claim 9 wherein in step "a" the two markers are attached to the outer peripheral wall portion of a blood vessel to be inspected at substantially one hundred eighty degrees (180°) apart.

11. The method of claim 6 wherein in step "a" two radiopaque discs are surgically attached by suturing to opposing outer wall portions of a blood vessel to be fluoroscopically inspected.

12. The method of claim 6 wherein the vessel to be fluoroscopically inspected is provided with the pair of spaced markers during a surgical operation.

13. A method of adapting a bypass graft blood vessel for subsequent fluoroscopic examination, comprising the steps of:
   a. surgically removing a blood vessel a patient to be used as a bypass;

b. attaching a pair of spaced radiopaque markers to the bypass blood vessel outer opposite wall portions; and c. surgically grafting the bypass blood vessel into a desired position with the grafted bypass vessel thereafter circulating blood.

14. The method of claim 13 further comprising the step "d" of fluoroscopically examining the pair of radiopaque markers to determine relative movement therebetween.

15. The method of claim 13 wherein in step 15 the pair of markers oscillate with respect to one another from a farther relative position to a closer relative position responsive to pulsatile blood flow through the graft vessel.

16. The method of claim 13 wherein in step "b" the radiopaque markers are surgically attached by suturing to the bypass vessel.

17. The method of claim 13 wherein in step "b" the pair of spaced radiopaqued markers are provided with differing indicia markers.

18. A method of adapting a bypass graft blood vessel for subsequent fluoroscopic examination comprising the steps of:

a. surgically removing a blood vessel from a patient to be used as a bypass graft vessel;

b. attaching at approximately one hundred eighty degrees (180°) apart a pair of spaced radiopaque markers to the bypass blood vessel outer wall surface portion, the pair of spaced markers being independently movable with respect to one another during pulsatile blood flow through the bypass blood vessel graft;

c. surgically grafting the bypass blood vessel into a desired position with the grafted bypass vessel thereafter adapted for circulating blood;

d. fluoroscopically examining the pair of radiopaque markers to determine relative movement therebetween, the examination determining relative outer vessel wall position and the presence of pulsatile blood flow through the graft.

19. A radiopaque coronary vessel marker apparatus comprising:

a. a pair of radiopaque marker discs adapted for surgical attachment to a portion of an interior blood vessel, said pair of discs indicating the pulsatile flow of blood through the blood vessel during, for example a coronary bypass operation, said radiopaque marker discs comprising each a marker body, said marker body providing an inner radiopaque member surrounded by an inert covering;

b. at least one opening through each marker body at said covering, said opening adapting each of said marker discs for surgical sutured attachment to a desired vessel to be marked.

20. The radiopaque vessel marker apparatus of claim 19 wherein said covering is an inert plastic resinous covering.

21. The radiopaque vessel marker apparatus of claim 19 wherein said marker discs are generally oval shaped.

22. The radiopaque vessel marker apparatus of claim 19, wherein there are two openings on each marker disc at opposite end portions thereof.

23. The radiopaque vessel marker apparatus of claim 19, wherein there is further provided suture means adapted for attachment to said marker bodies at said openings, said suture means being provided with a needle for attaching said suture means and said associated discs to a vessel to be marked.

24. A radiopaque vessel marker apparatus for indicating vessel pulsatile blood flow comprising:

a. first radiopaque oval marker disc, said marker disc having a pair of suture attachment openings at its opposite end portions;

b. a second radiopaque oval marker disc, said second marker disc having a pair of openings at its opposite end portions, said openings adapted for receiving surgical suture therethrough for attaching said marker disc to a vessel to be marked, said first and said second radiopaque markers each comprising a central inner radiopaque member and a surrounding and embedding outer covering, said covering being an inert plastic material, each of said markers providing upper and lower surfaces, said lower surface of each marker disc being adapted for attachment to the surface portion of a vessel to be marked, said radiopaque member adapting each of said discs for fluoroscopic examination; and c. surgical suture attachment means associated with each of said openings on each of said markers for attaching said markers to a blood vessel to be marked, said surgical suture means being adapted for atttachment to a surgical needle during operation.

25. The radiopaque vessel marker apparatus of claim 24 wherein said radiopaque member is a tantilum metal material.

* * * * *